(12) United States Patent
Da Costa

(10) Patent No.: US 8,114,292 B2
(45) Date of Patent: Feb. 14, 2012

(54) METHOD AND MICRO-ORGANISM FOR TREATING WASTE WATER

(75) Inventor: Alexandre Da Costa, Savigny le Temple (FR)

(73) Assignee: Eco Solution, Romainville (FR)

( * ) Notice: Subject to any disclaimer, the term of this patent is extended or adjusted under 35 U.S.C. 154(b) by 568 days.

(21) Appl. No.: 12/298,764

(22) PCT Filed: Apr. 20, 2007

(86) PCT No.: PCT/FR2007/000669
§ 371 (c)(1),
(2), (4) Date: Oct. 27, 2008

(87) PCT Pub. No.: WO2007/128897
PCT Pub. Date: Nov. 15, 2007

(65) Prior Publication Data
US 2009/0071898 A1    Mar. 19, 2009

(30) Foreign Application Priority Data

Apr. 27, 2006  (FR) ..................... 06 03792

(51) Int. Cl.
*C02F 3/00*    (2006.01)

(52) U.S. Cl. ........ 210/611; 210/615; 210/616; 210/620; 435/252.1; 435/252.4; 435/170

(58) Field of Classification Search ............... 435/252.1, 435/252.4, 170; 210/611, 615–616, 620–628
See application file for complete search history.

(56) References Cited

FOREIGN PATENT DOCUMENTS
GB     2030557 A    10/1978

OTHER PUBLICATIONS

Joo Hung-Soo et al: "Novel Microorganism for Treating Wastewater and Corresponding Method" by *Alcaligenes faecalis* vol. 27, No. 11, Jun. 2005, pp. 773-778.

*Primary Examiner* — Chester Barry
(74) *Attorney, Agent, or Firm* — Browdy and Neimark, PLLC

(57) ABSTRACT

The invention concerns a novel isolated microorganism characterized in that it is capable of: i) transforming Kjeldahl nitrogen, ammonia nitrogen and/or nitrogen oxides into gas nitrogen; and ii) transforming carbonaceous matter into carbon dioxide; both transformation processes being carried out in aerobic condition. The invention also concerns a method for treating wastewater using said microorganism.

25 Claims, No Drawings

METHOD AND MICRO-ORGANISM FOR TREATING WASTE WATER

TECHNICAL FIELD

The present invention relates to the field of wastewater pollution control.

In particular it relates to the isolation and characterization of a novel microorganism capable of converting the carbonaceous matter and the nitrogenous matter under aerobic conditions. This microorganism is particularly useful for the biological treatment of carbon- and nitrogen-loaded effluents.

PRIOR ART

Biological treatment of carbonaceous and nitrogenous matter currently uses at least two types of microorganisms, the first specialized in the treatment of the carbonaceous matter, the second specialized in the treatment of the nitrogenous matter.

In fact, pollution control of the organic matter generally takes place in activated-sludge tanks in which the carbonaceous matter is converted to biomass and carbon dioxide under aerobic conditions. Alternatively, the organic matter can be converted to biomass and methane under aerobic conditions.

After either of these treatments, the nitrogen load of the effluents being treated remains high. Treatment of the nitrogen load requires a later stage involving specialized microorganisms.

Various methods are currently used to convert the nitrogen contained in ammoniacal ($NH_3$) or oxidized ($NO_2^-$, $NO_3^-$) form in the aqueous effluents to gaseous nitrogen ($N_2$).

Currently, the most widely-used treatment is constituted by a stage of aerobic nitrification followed by a stage of anoxic denitrification.

Nitrification consists of the oxidation of the ammoniacal nitrogen ($NH_3$) to nitrites ($NO_2^-$) using autotrophic bacteria including, for example, species from the genera *Nitrosomonas, Nitrosospira* and *Nitrosococcus*, then oxidation of the nitrites previously produced to nitrates ($NO_3^-$) using autotrophic bacteria including for example species from the genera *Nitrobacter, Nitrococcus* and *Nitrospira*.

Denitrification consists of reduction of the oxidized forms of the mineral nitrogen (nitrites ($NO_2^-$), nitrates ($NO_3^-$)) to gaseous compounds ($N_2$), by a denitrifying functional microbial population, most of the time heterotrophic, in the presence of an electron donor. This method is carried out by many bacteria including, for example, species belonging to the genera *Pseudomonas, Bacillus, Paracoccus, Thiobacillus, Alcaligenes*. Reduction of the oxidized forms of the nitrogen is therefore coupled to the oxidation of an organic compound. This means that carbon is a factor limiting the denitrification. In fact, if the aqueous effluents for treatment have a carbonaceous matter concentration which is insufficient to support the activated microbial populations vis-à-vis the nitrogen treatment, the addition of an exogenous source of carbon can prove necessary for the satisfactory operation of the denitrification reactors. This is the case, in particular, if the effluent for treatment has a low carbon load (Carbon/Nitrogen ratio (C/N)<4), or if it undergoes a primary settlement before denitrification.

Denitrification can be carried out by treating the effluent collected after the nitrification stage in an anoxia tank containing the denitrifying bacteria.

According to another mode of operation, the nitrification tank can be used periodically as a denitrification tank, by making it anoxic, for example by interrupting the oxygen supply and by adding electron donors, among which methanol is the one most often used.

Among the drawbacks of this nitrification-denitrification method, it will be noted that the autotrophic nitrifying strains have a low growth rate. This kinetic characteristic imposes long periods spent in the tanks, resulting in the need either to design large-scale constructions, or to extend the treatment line with new constructions, involving high investment costs. Moreover, in the case of a stage of denitrification carried out in an additional tank, it is necessary to supply a source of organic carbon to the denitrifying flora, such as methanol, which may incur additional operating costs.

Another treatment method for ammoniacal nitrogen called Anammox (for Anaerobic Ammonia Oxidation) allows bioconversion of the ammoniacal nitrogen and nitrites into gaseous nitrogen. This reaction can be carried out by treating the nitrification effluent (containing nitrites and unreacted ammonium) in a separate tank to produce gaseous nitrogen. According to another mode of operation, the nitrification tank can be run alternately under oxic and anoxic conditions, or continuously under limited-oxygen conditions. In this case, the consumption of oxygen by the nitrifying bacteria generates the anoxic conditions for the Anammox process. The bacteria capable of catalyzing the Anammox reaction can be obtained from conventional activated sludges, to the extent that the latter contain planctomycete bacteria of the *Brocardia anammoxidans* type.

The main drawback of the Anammox method is the low growth rate of the planctomycete bacteria used, involving long installation start-up phases. Moreover, it remains difficult to culture these bacteria and to maintain them in pure cultures. Finally, partial nitrification (conversion of 50% of the ammonia to nitrites) must be perfectly controlled, which is difficult to carry out under actual operating conditions.

The Sharon method located upstream of the Anammox treatment allows a partial nitrification to be obtained. The Sharon method is based on the difference which exists between the growth rate of the bacteria oxidizing the ammonia and that of the bacteria oxidizing the nitrites. This treatment operates with a hydraulic retention time less than the growth rate of the bacteria oxidizing the nitrites, but greater than that of the bacteria oxidizing the ammonia (approximately one day). Since there is no sludge retention, the bacteria oxidizing the nitrites are not maintained in the reactor and are therefore eliminated.

Recently, strains of *Alcaligenes faecalis* have been identified as being capable of carrying out nitrification and denitrification under aerobic conditions. This is the case with the strain *Alcaligenes faecalis* sp. No. 4 described in the article by Joo et al. (Biotechnology Letters (2005) 27:773-778). Using such a strain, the treatment of the ammoniacal nitrogen can be carried out in a single aerobic stage.

However, this bacterium does not make it possible to convert all of the ammoniacal nitrogen to gaseous nitrogen. In fact, significant quantities of intermediate products of denitrification accumulate. Thus, in the best case, the treatment of high levels of ammonium based on the use of *Alcaligenes faecalis* sp. No. 4 under aerobic conditions, with a C/N ratio of 10, leads to the elimination of 40-50% of the $NH_4^+$ by denitrification and 90% of the products of denitrification are gaseous nitrogen. On the other hand, this bacterium functions optimally with high C/N ratios, requiring an addition of carbon to the effluent to be treated (Joo et al. (2005)).

As a result, the improvement in the performances of the treatment of the ammoniacal nitrogen in wastewater now uses the addition of specific treatments called tertiary treatments, with activated sludges or biofilters, to existing installations. The equipment and constructions necessary to carry out these treatments represent high levels of investment and also generate significant operating costs when it becomes necessary to add carbonaceous substrates for example during denitrification.

The present invention aims to remedy the drawbacks of the prior art and describes a method for the biological treatment of the carbonaceous matter and of the nitrogen in Kjeldahl, ammoniacal or oxidized form within a single aerobic stage by heterotrophic microorganisms having a high growth rate which makes it possible to design purification installations of reduced size.

The invention also aims to obtain a reduction in the operating costs of the purification plants in particular those which use denitrification tanks located downstream of the nitrification tanks. In fact, since the ammoniacal nitrogen is converted to gaseous nitrogen in the aeration tanks, the anoxic denitrification tanks located downstream are no longer of any use.

The savings produced therefore result on the one hand from omission of the addition of organic carbonaceous substrate (methanol type), and on the other hand, from the reduction in sludge production by elimination of the anoxic treatment stage.

The invention therefore allows optimum operation of the existing water-treatment without requiring complementary treatment stages.

DESCRIPTION OF THE INVENTION

In this context, the applicant has isolated a novel microorganism capable of converting the carbonaceous matter and the nitrogenous matter under aerobic conditions which makes it particularly useful in the treatment of wastewater.

The nitrogenous matter converted by the microorganism according to the invention can be Kjeldahl nitrogen, ammoniacal nitrogen and/or nitrogen oxides.

The Kjeldahl nitrogen comprises nitrogen in the organic form and in the ammoniacal form to the exclusion of the nitrous forms (nitrites, nitrates).

This is why a first subject of the invention relates to an isolated microorganism characterized in that it is capable of achieving:

i) the conversion of Kjeldahl nitrogen, ammoniacal nitrogen and/or nitrogen oxides to gaseous nitrogen; and ii) the conversion of carbonaceous matter to carbon dioxide;

the two conversions taking place under aerobic conditions.

In a preferred manner, the microorganism according to the invention is capable of converting the Kjeldahl nitrogen, ammoniacal nitrogen and/or nitrogen oxides to gaseous nitrogen accumulating less that 1% nitrogen oxides.

Also in a preferred manner, the microorganism according to the invention is capable of bringing about the conversion of the Kjeldahl nitrogen, ammoniacal nitrogen and/or nitrogen oxides to gaseous nitrogen while accumulating less than 1% nitrogen oxides, said conversion being optimum when the C/N ratio of the medium is less than 4, preferably less than 3, preferably of the order of 1.5.

The microorganism according to the invention is capable of carrying out the conversion of the Kjeldahl nitrogen, ammoniacal nitrogen and/or nitrogen oxides to gaseous nitrogen under conditions of applied loading (AL) less than 0.2 $kg_{BOD5}/kg_{VMS}/d$.

A microorganism isolated as described previously is more particularly preferred, characterized in that it converts Kjeldahl nitrogen, ammoniacal nitrogen and/or nitrogen oxides under applied loading (AL) conditions greater than or equal to 0.2 $kg_{BOD5}/kg_{VMS}/d$, preferably greater than 0.5 $kg_{BOD5}/kg_{VMS}/d$.

The microorganism according to the invention belongs preferentially to the genus *Alcaligenes*, in particular to the species *Alcaligenes faecalis*.

In a yet more preferred manner, the microorganism according to the invention is represented by the strain *Alcaligenes faecalis* deposited on 10 Jun. 2005 at the Collection Nationale of Cultures of Microorganisms at the Institut Pasteur (CNCM) under reference CNCM I-3448.

The invention extends to the microorganism derived from the strain CNCM I-3448, having the ability to convert carbonaceous matter and nitrogenous matter under aerobic conditions.

By derived microorganism is meant any microorganism originating from the strain CNCM I-3448 which could result, for example, from a stage of culture, mutation, conversion of the strain CNCM I-3448 or even of its crossing with another microorganism, and which would have retained the essential characteristics of the strain CNCM I-3448.

Another subject of the invention is the use of the microorganism according to the invention for the treatment of wastewater.

The preferred use of the microorganism according to the invention relates to the conversion of the Kjeldahl nitrogen, ammoniacal nitrogen and/or nitrogen oxides contained in the wastewater to gaseous nitrogen, under aerobic conditions.

According to an aspect of the use according to the invention, less than 1% of nitrogen oxides ($NO_3^-$, $NO_2^-$) accumulate.

In a yet more preferred manner, the use of the microorganism according to the invention relates to the combined treatments of the Kjeldahl nitrogen, ammoniacal nitrogen and/or nitrogen oxides and the carbonaceous matter contained in the wastewater, under aerobic conditions.

In particular, during the use according to the invention, the Kjeldahl nitrogen, ammoniacal nitrogen and/or nitrogen oxides are converted to gaseous nitrogen and the carbonaceous matter is converted to carbon dioxide.

The use according to the invention can be carried out under conditions where the applied load (AL) of the medium is less than 0.2 $kg_{BOD5}/kg_{VMS}/d$.

Preferably, the use according to the invention is carried out under conditions where the applied load (AL) is greater than 0.2 $kg_{BOD5}/kg_{VMS}/d$, in a yet more preferred manner greater than 0.5 $kg_{BOD5}/kg_{VMS}/d$.

According to a preferred embodiment of the use according to the invention, no external carbonaceous source is added to the wastewater for treatment.

One of the preferred characteristics of the use according to the invention is that the combined treatments of the Kjeldahl nitrogen, ammoniacal nitrogen and/or nitrogen oxides and carbonaceous matter contained in the wastewater take place in a single free activated sludge tank.

Alternatively, the use according to the invention is characterized by the fact that the combined treatments of the Kjeldahl nitrogen, ammoniacal nitrogen and/or nitrogen oxides and carbonaceous matter contained in the wastewater take place in a culture device fixed onto a support.

According to another aspect, the invention relates to the use of a microorganism as described previously, produced by continuous culture beforehand. Preferably, said continuous culture is carried out under sterile conditions. In a yet more preferred manner, said continuous culture is carried out under a selective pressure and for indefinite periods.

Another subject of the invention relates to a wastewater treatment method characterized in that it utilizes a microorganism as described previously.

According to an aspect of the invention, the wastewater treatment method comprises the following stages:

i) the culture of the microorganism as described previously;

ii) the automatic supply of a treatment device containing the wastewater for treatment by repeated inputs of the culture produced in stage i); and iii) the biological treatment of the carbonaceous matter and nitrogenous matter contained in the wastewater, within the treatment device, under aerobic conditions.

According to an aspect of the invention, the biological treatment of the carbonaceous matter and the biological treatment of the nitrogenous matter of stage iii) take place simultaneously.

In a preferred manner, the wastewater treatment device mentioned in stages ii) and iii) is an aeration tank.

A subject of the invention is also the control of the effectiveness of the biological pollution control of the wastewater in order to optimize the treatment of the effluents as a function of the constraints, for example, the increase in carbonaceous and or nitrogenous load.

Also, in a yet more preferred manner, the activity of the microorganism according to the invention present within the free activated sludges in the aeration tank according to one of the methods described above is evaluated by regular transfers of samples to a culture device then compared with a culture of said microorganism maintained under selective pressure.

According to another embodiment, the method according to the invention comprises, in parallel, aerobic conversions of the Kjeldahl nitrogen, ammoniacal nitrogen and/or nitrogen oxides and carbonaceous matter by the microorganism according to the invention in the treatment device, the continuous culture of the microorganism according to the invention in a medium containing nutrients (source of carbon, source of nitrogen etc.) necessary for microbial growth in order to periodically inoculate the treatment device with said microorganism.

Preferentially, the microbial growth is carried out in a device making it possible to culture the microorganism according to the invention under sterile culture conditions. More particularly, this culture is carried out under selective pressure and for indefinite periods.

According to a particular embodiment of the invention, this parallel culture is used to regularly seed an amplification reactor having a volume of a few hundred litres to a few cubic metres, in which a culture of the microorganism according to the invention is produced in a non-sterile fashion in a significant quantity. The culture medium can be synthetic or consist of an effluent for treatment and must be sufficiently selective to promote the significant production of said microorganism. Repeated inputs of this culture can be carried out automatically according to a defined frequency to the wastewater treatment device, for example the free activated sludge aeration tank. No organic substrate such as for example methanol is added to the treatment device to promote the maintenance of the microorganism according to the invention given that the latter uses the organic matter present in the wastewater for treatment as a source of carbon.

Alternatively, in an advantageous manner, the wastewater treatment device mentioned in stages ii) and iii) is a culture device fixed on a support.

According to another aspect of the method according to the invention, said method comprises, upstream of the treatment device, a stage for evaluating the toxicity of the incoming wastewater vis-à-vis the microorganism. The toxicity evaluation stage can be based, in particular, on measurement of the growth of said microorganism on said wastewater.

A effluent which is toxic to the microorganism, and therefore detrimental to the conversion of the Kjeldahl nitrogen, ammoniacal nitrogen and/or nitrogen oxides to gaseous nitrogen, could then be directed towards a safety tank for subsequent treatment.

According to another aspect of the invention, the microorganism is fixed onto a support.

Said support can contain a structured or other type of lining, making it possible to optimize the implantation of the cultured population of the microorganism according to the invention, its fixation and its development under favourable conditions. This lining can be of different types and of different materials known to a person skilled in the art.

In particular, the microorganism according to the invention is fixed alone or in co-culture with one or more microorganisms specialized in the treatment of carbonaceous pollution.

The distribution of the microorganism according to the invention on the surface of the support must be the best possible and the satisfactory development of the method depends on transfers between the microorganisms and the effluent for treatment. In terms of aeration, the installation must be designed such that the transfer of oxygen is as effective as possible for the purifying microorganisms fixed on the support. On the other hand, a good transfer of the effluent towards the fixed microorganisms is needed, with respect to the pollutants for treatment (in particular Kjeldahl nitrogen, ammoniacal nitrogen and/or nitrogen oxides and carbonaceous matter), and in the opposite direction for the metabolism products of the microorganisms (in particular carbon dioxide and gaseous nitrogen).

According to the invention, the wastewater for treatment includes any sewage, whether municipal, industrial, agricultural or of any other origin, which contains significant levels of ammoniacal nitrogen. The level Kjeldahl or ammoniacal nitrogen in the effluent for treatment is, for example, 50 mg/l, in particular 1 g/l, particularly 30 g/l. The wastewater for treatment can also originate from the water used for purifying the gas containing ammoniacal nitrogen.

The method according to the invention is particularly suited to the treatment of wastewater containing more than 30 g/l of Kjeldahl nitrogen or ammoniacal nitrogen.

The wastewater for treatment also contains significant levels of organic carbon. The total organic carbon contents can be, for example, 80 mg/l, in particular 1 g/l, particularly 80 g/l or 95 g/l.

According to another aspect, the method according to the invention is accompanied by the accumulation of less than 1% nitrogen oxides ($NO_2^-$, $NO_3^-$).

The examples which follow illustrate the invention but should not be considered as limitative.

Example 1

Bioconversion of an Urban Synthetic Effluent

A 1-litre fermenter is continuously fed with a synthetic effluent having the average composition of wastewater of urban origin. The composition of this effluent is as follows: 53 mg/l of N—$NH_3$ in the form of $(NH_4)_2SO_4$, 82 mg/l of total organic carbon (TOC) in the form of sodium acetate, 0.1 g/l of $K_2HPO_4$ and trace elements known to a person skilled in the art for promoting the growth of these microorganisms. The pH of the solution is adjusted to 8 with HCl/NaOH if necessary.

The fermenter contains a pure culture of the strain *Alcaligenes faecalis* CNCM I-3448.

Continuous operation is maintained by fixing an applied volumetric load of 1.9 g $NH_3/m^3/d$ and 2.6 g $C/m^3/d$.

This embodiment corresponds to conditions where the applied load (AL) is 0.27 $kg_{BOD5}/kg_{VMS}/d$ and the C/N ratio of the medium is 1.5.

Aeration of the culture is ensured by bubbling compressed air through (dissolved oxygen concentration greater than 3 mg/l). The single air outlet is linked to a bubbler containing 2 litres of osmosis-purified water at pH 5. The purpose of this assembly is to ensure that ammonia is not evacuated by the aeration during the continuous biodegradation of the effluent.

When the stabilized state is reached, the concentration of ammonia in the bubbler (pH 5) is zero, the average concentration of dry matter is 0.7 g/l, 90% the incoming carbon (TOC) is converted either to biomass or to carbon dioxide.

A reduction of 99.9% in the ammoniacal nitrogen is measured, which is converted either to biomass or to gaseous nitrogen. The bioconversion yield of the nitrogen obtained is therefore greater than 99.9%.

Moreover, no accumulation of nitrites and nitrates is measured in the medium, nor in the effluent output.

Example 2

Bioconversion of Concentrated Industrial Effluents with Organic Nitrogen

A 7.5-litre fermenter is continuously fed with wastewater essentially comprising nitrogenous solvents (such as acetonitrile or dimethylformamide) originating from the production of peptides.

Analysis of the effluent reveals a total organic carbon (TOC) concentration of 95 g/l and a Kjeldahl nitrogen concentration of 34 g/l (essentially originating from the acetonitrile).

The fermenter contains a pure culture of the strain *Alcaligenes faecalis* CNCM I-3448.

Continuous operation is maintained by fixing an applied volumetric load of 1.2 kg $N/m^3/d$ and 3.2 kg $C/m^3/d$.

This embodiment corresponds to conditions where the applied load (AL) is 0.96 $kg_{BOD5}/kg_{VMS}/d$ and the C/N ratio of the medium is 2.8.

The air entering the culture (8 l/min) passes through a humidifier. The single air outlet is connected to a bubbler containing 2 litres of osmosis-purified water at pH 5. The purpose of this assembly is to ensure that Kjeldahl nitrogen is not evacuated by the aeration during the continuous biodegradation of the effluent. It is observed that the flow of Kjeldahl nitrogen in the gaseous effluents represents one-tenth of the incoming flow.

When the stabilized state is reached, the Kjeldahl nitrogen concentration in the bubbler (pH 5) is zero, the average concentration of dry matter is 10 g/l, 98% of the incoming carbon (TOC) is converted either to biomass or to carbon dioxide.

A 99.9% reduction in the Kjeldahl nitrogen is measured, which is converted either to biomass or to gaseous nitrogen.

Moreover, the accumulation in the medium and in the effluent output of oxidized forms of nitrogen ($NO_2$ and $NO_3$) is less than 1% and temporary (<12 h).

The bioconversion yield of the Kjeldahl nitrogen obtained is therefore greater than 99%.

The invention claimed is:

1. An isolated microorganism of the strain CNCM I-3448 *Alcaligenes faecalis* or microorganisms derived from said strain that it is capable of achieving:
   i) the conversion of Kjeldahl nitrogen, ammoniacal nitrogen and/or nitrogen oxides to gaseous nitrogen; and
   ii) the conversion of the carbonaceous matter to carbon dioxide; the two conversions taking place under aerobic conditions.

2. The isolated microorganism according to claim 1, wherein it converts Kjeldahl nitrogen, ammoniacal nitrogen and/or nitrogen oxides under applied loading (AL) conditions greater than or equal to 0.2 $kg_{BOD5}/kg_{VMS}/d$.

3. The isolated microorganism according to claim 1, wherein it converts Kjeldahl nitrogen, ammoniacal nitrogen and/or nitrogen oxides under applied loading (AL) conditions greater than 0.5 $kg_{BOD5}/kg_{VMS}/d$.

4. The microorganism according to claim 1, wherein it converts Kjeldahl nitrogen, ammoniacal nitrogen and/or nitrogen oxides to gaseous nitrogen while accumulating less than 1% nitrogen oxides.

5. The microorganism according to claim 1, wherein it converts Kjeldahl nitrogen, ammoniacal nitrogen and/or nitrogen oxides to gaseous nitrogen in an optimum manner when the C/N ratio in the medium is less than 4, preferably less than 3, in a yet more preferred manner of the order of 1.5.

6. A wastewater treatment method which utilizes a microorganism according to claim 1.

7. The wastewater treatment method according to claim 6 for the conversion of Kjeldahl nitrogen, ammoniacal nitrogen and/or nitrogen oxides contained in the wastewater to gaseous nitrogen, under aerobic conditions.

8. The wastewater treatment method according to claim 7 for the combined treatments of Kjeldahl nitrogen, ammoniacal nitrogen and/or nitrogen oxides and the carbonaceous matter contained in the wastewater, under aerobic conditions.

9. The wastewater treatment method according to claim 8, wherein Kjeldahl nitrogen, ammoniacal nitrogen and/or nitrogen oxides are converted to gaseous nitrogen and the carbonaceous matter is converted to carbon dioxide.

10. The wastewater treatment method according to claim 8, wherein the applied load (AL) is greater than 0.2 $kg_{BOD5}/kg_{VMS}/d$.

11. The wastewater treatment method according to claim 10, wherein the applied load (AL) is greater than 0.5 $kg_{BOD5}/kg_{VMS}/d$.

12. The wastewater treatment method according to any one of claim 6 and 7 to 11, wherein no external carbonaceous source is added to the wastewater for treatment.

13. The wastewater treatment method according to claim 6, wherein the treatments take place in a single free activated sludge tank.

14. The wastewater treatment method according to claim 6, wherein the treatments take place in a culture device fixed on a support.

15. The wastewater treatment method according to claim 6, wherein the microorganism is produced by continuous culture beforehand.

16. The wastewater treatment method according to claim 15, wherein the continuous culture of the microorganism is carried out under sterile conditions.

17. The wastewater treatment method according to claim 16, wherein the continuous culture of the microorganism is carried out under selective pressure and for indefinite periods.

18. The wastewater treatment method according to claim 6 comprising the following stages:
   i) culture of the microorganism, wherein the microorganism is capable of achieving:
      i) the conversion of Kjeldahl nitrogen, ammoniacal nitrogen and/or nitrogen oxides to gaseous nitrogen; and ii) the conversion of the carbonaceous matter to carbon dioxide; the two conversions taking place under aerobic conditions;

ii) the automatic supply of a treatment device containing the wastewater for treatment by repeated inputs of the culture produced in stage i); and iii) the biological treatment of the carbonaceous matter and nitrogenous matter contained in the wastewater, within the treatment device, under aerobic conditions.

19. The wastewater treatment method according to claim 18, in which the biological treatment of the carbonaceous matter and the biological treatment of the nitrogenous matter of stage iii) take place simultaneously.

20. The method according to claim 18, in which the wastewater treatment device is a free activated sludge aeration tank.

21. The method according to claim 18, in which the wastewater treatment device is in a culture device fixed on a support.

22. The method according to claim 6, comprising upstream of the treatment device a stage for evaluating the toxicity of the incoming wastewater vis-à-vis the microorganism.

23. The method according to claim 6, in which the microorganism is fixed on a support.

24. The method according to claim 23, in which the microorganism is fixed alone or in co-culture with one or more microorganisms specialized in the treatment of carbonaceous pollution.

25. The method according to claim 6, in which the wastewater for treatment contains more than 30 g/l of Kjeldahl nitrogen or ammoniacal nitrogen.

* * * * *